(12) United States Patent
Embleton et al.

(10) Patent No.: US 9,622,802 B2
(45) Date of Patent: Apr. 18, 2017

(54) QUADRUPED STIFLE STABILIZATION SYSTEM

(71) Applicant: Embark Enterprises Inc., Sundre (CA)

(72) Inventors: Neil Embleton, Sundre (CA); Veronica Barkowski, Sundre (CA)

(73) Assignee: Embark Enterprises, Inc., Sundre, AB (CA)

( * ) Notice: Subject to any disclaimer, the term of this patent is extended or adjusted under 35 U.S.C. 154(b) by 0 days.

(21) Appl. No.: 15/156,839

(22) Filed: May 17, 2016

(65) Prior Publication Data

US 2016/0256205 A1   Sep. 8, 2016

Related U.S. Application Data

(63) Continuation-in-part of application No. 14/203,266, filed on Mar. 10, 2014.

(60) Provisional application No. 61/776,735, filed on Mar. 11, 2013, provisional application No. 61/778,324, filed on Mar. 12, 2013.

(51) Int. Cl.
| | |
|---|---|
| *A61B 17/56* | (2006.01) |
| *A61B 17/58* | (2006.01) |
| *A61B 17/80* | (2006.01) |
| *A61F 2/30* | (2006.01) |
| *A61F 2/38* | (2006.01) |
| *A61D 1/00* | (2006.01) |

(52) U.S. Cl.
CPC .......... *A61B 17/8061* (2013.01); *A61B 17/56* (2013.01); *A61B 17/8023* (2013.01); *A61D 1/00* (2013.01); *A61F 2/389* (2013.01); *A61F 2/3854* (2013.01); *A61F 2/3859* (2013.01); *A61F 2/3886* (2013.01); *A61B 2017/567* (2013.01)

(58) Field of Classification Search
None
See application file for complete search history.

(56) References Cited

U.S. PATENT DOCUMENTS

2004/0102776 A1* 5/2004 Huebner ............ A61B 17/1728
606/281

* cited by examiner

*Primary Examiner* — Sameh Boles
(74) *Attorney, Agent, or Firm* — McCarter & English, LLP

(57) ABSTRACT

A stifle stabilization system is provided herein. The system comprising a femoral component having a leg portion and bottom portion, the bottom portion including an interconnected coupling member protruding therefrom, an articular sliding insert component having a channel corresponding in size and shape to at least part of the coupling member, an enlarged opening in a bottom surface of the insert component in communication with the channel, and a slot through the bottom surface of the insert component in communication with the enlarged opening and the channel, the channel receiving the at least part of the coupling member through the enlarged opening, and a tibial component having a first proximal planar portion defining a slot, the slot being of corresponding and complementary shape to the articular sliding insert component to receive the articular sliding insert component therein.

23 Claims, 15 Drawing Sheets

QUADRUPED STIFLE STABILIZATION SYSTEM

CROSS-REFERENCE TO RELATED APPLICATIONS

This application is a continuation-in-part of, and claims the benefit of U.S. patent application Ser. No. 14/203,266, filed on Mar. 10, 2014, which claims the benefit of U.S. Provisional Patent Application No. 61/776,735, filed on Mar. 11, 2013 and U.S. Provisional Patent Application No. 61/778,324, filed on Mar. 12, 2013, the entire disclosures of which are expressly incorporated herein by reference.

BACKGROUND OF THE INVENTION

Technical Field

The present invention relates to a method and apparatus for veterinary orthopedic surgical stabilization of an unstable quadruped stifle joint.

Related Art

The quadruped stifle is a complex and powerful joint that is stabilized by four main ligaments (e.g., the cranial cruciate, the caudal cruciate, the medial collateral, and the lateral collateral). The stifle joint is further stabilized by the patella and the tendons associated therewith and the surrounding musculature. These powerful ligaments and tendons bind the femur and tibia together. Although the structure of the stifle provides one of the strongest joints of the quadruped body, as in humans, the stifle joint is also one of the most frequently injured joints. The most frequent injury occurs to the cranial cruciate ligament.

The canine is the most frequently affected quadruped species. The large number of canine cranial cruciate ligament injuries has given rise to a considerable number of innovative surgical procedures and devices for attempting to replace the partially or completely torn or avulsed cranial cruciate ligament. A partially, or completely torn, stifle associated ligament or tendon typically results in serious clinical symptoms (e.g., stifle swelling and inflammation, significant stifle pain, disuse muscular atrophy, radiographic evidence of arthritis and stifle joint instability, etc.) resulting in a significantly diminished ability to perform high level, or daily activities relating to mobility. The inevitable long term effects of a damaged and unstable quadruped stifle joint include significant meniscal and articular cartilage damage to the femur, tibia, and patella. This leads to chronic pain and debilitating degenerative joint disease.

Injury (or disruption) of any of the ligaments or tendons (including the cranial cruciate ligament) of the quadruped stifle typically requires a major surgical intervention to address the injury. Historically and currently these attempts at repair have involved both intra-articular and extra-articular repair procedures with varying degrees of success. More recently geometric modification of the canine stifle joint has been advocated.

Several types of surgical procedures have been developed and are currently in use to attempt to mitigate the instability of the canine stifle caused by the damaged cranial cruciate ligament and/or other ligaments and tendons. Although primary cranial cruciate ligament repair would be ideal, it is unfortunately not a viable option in veterinary medicine for a number of reasons (e.g., cranial cruciate injury in quadrupeds is rarely acute, the injury is usually a chronic injury/disease that progresses over time and the amount of trauma that occurs to the cranial cruciate ligament is usually very severe). As a result the torn ends of the cranial cruciate ligament are not of a sufficient length to reattach successfully or have been resorbed to an extent that reattachment is not possible.

Historically intra-articular stabilization of the cranial cruciate deficient canine stifle was performed via placement of an autogenous graft, harvested either from the patella tendon or the tensor fascia lata. This method involved harvesting of the graft and then tunnelling the graft through the stifle joint and attaching so that it mimics the cranial cruciate ligament. This method has fallen out of favor due to the invasiveness of the surgical procedure required, the inherent weakness of the graft and high rate of failure of the autogenous grafting material.

Other current techniques, although purported to be extracapsular (e.g., outside the joint) repair methods are actually intracapsular repair methods. Numerous terms and techniques are utilized. One technique utilizes a synthetic nylon (e.g., commercial fishing line) or a braided polymer material to prevent cranial tibial thrust. These materials both generally ultimately fail to prevent cranial tibial thrust. The nylon material cycles, weakens, and either stretches or breaks due to movement of the stifle joint, or will tear through the surrounding soft tissues. The braided polymer material, while much stronger, either breaks, cuts through the bone, or as a result of being braided, becomes infected. These current techniques have been successful in reducing abnormal femoral/tibial movement in a sagittal plane. However, neither of these current extra-capsular repair techniques permits the tibia, in relation to the femur, to internally and externally rotate as in a normal joint, nor do they permit normal compression and extension. These techniques also cause a valgus deformation of the tibia relative to the femur.

Another class of cranial cruciate repair surgery is the geometric modification of the quadruped stifle joint, which relied upon the idea that the stifle joint would be dynamically stabilized by altering either the slope of the proximal tibia, or the position of the tibial tuberosity. There are currently two accepted geometric modification procedures (e.g., the tibial plateau leveling surgical osteotomy (TPLO) of the proximal tibia and tibial tuberosity advancement (TTA)). The TPLO procedure involves a full thickness semi-circular osteotomy below the proximal tibia. The proximal portion of the tibial bone is then rotated counterclockwise to decrease the tibial slope and therefore, associated cranial tibial thrust. The rotated bone is fixed in place using a specialized bone plate. The TTA procedure involves an angled, vertical cut of the tibial tuberosity. The freed portion is then advanced and fixed into place using specialized bone plating equipment. Both procedures require a very invasive surgical procedure that accomplishes its goal of decreasing cranial tibial thrust by either, transposing or rotating the cut proximal piece of tibia.

The current issues surrounding these repair methods center around the requirement that either the caudal cruciate (TPLO) or the central patellar tendon (TTA) is required to act as the cranial cruciate ligament, which is a task that neither tissue was designed to do. Other issues with geometric repair methods include the limited access of veterinarians capable of performing the procedures due to the specialized training and expensive equipment required for both the TPLO and TTA procedures. These procedures have been purported to dynamically stabilize the unstable stifle joint, but new research indicates that this is simply not the case and that the stifle joint remains unstable for a large portion of the stride. These procedures also do not limit the internal rotation of the tibia relative to the femur, which is one of the primary jobs of the quadruped, cranial cruciate ligament. This is particularly important when considering that during certain parts of the stride, the quadruped stifle joint is non-weight bearing and unsupported. It is during this non-weight bearing period that internal rotation of the tibia is unrestricted greatly increasing the risk that additional quadruped stifle joint trauma can, will, and does, occur at this time.

Other ligament or tendon injuries to the quadruped stifle require different procedures to repair the damage. Many of these procedures have varying success rates.

To date no one procedure exists to stabilize unstable, injured, and fractured quadruped stifles. Accordingly, what is needed is a method of providing continuous support to the damaged, quadruped stifle during both non weight bearing and full weight bearing phases of the stride.

SUMMARY

A surgical procedure and apparatus is provided for biocompatible, extracapsular, modular surgical stifle stabilization that can be permanently, or temporarily, surgically implanted on the medial side of the distal femur and proximal tibia to stabilize an unstable, quadruped, stifle joint. The system provides continuous resistance to abnormal cranial or caudal tibial thrust while not interfering with normal movement of the quadruped stifle.

The apparatus provides continuous support to the injured quadruped stifle, while permitting the quadruped stifle to move in a normal manner during all phases of the quadruped stride. The apparatus offers continuous support and permits normal flexion and extension, normal internal and external rotation, normal compression and expansion of the quadruped stifle joint during all phases of the stride. This procedure and apparatus could be used for a cranial cruciate rupture, caudal cruciate rupture, medial collateral rupture, lateral collateral rupture, medial patellar luxation, lateral patellar luxation, patellar tendon avulsion, patellar fracture, proximal tibial fracture, distal femoral fracture, stifle disruption, and any combination thereof, or any degree of any of the above conditions.

BRIEF DESCRIPTION OF THE DRAWINGS

The foregoing features of the disclosure will be apparent from the following Detailed Description of the Disclosure, taken in connection with the accompanying drawings, in which.

DETAILED DESCRIPTION

Figure 1:
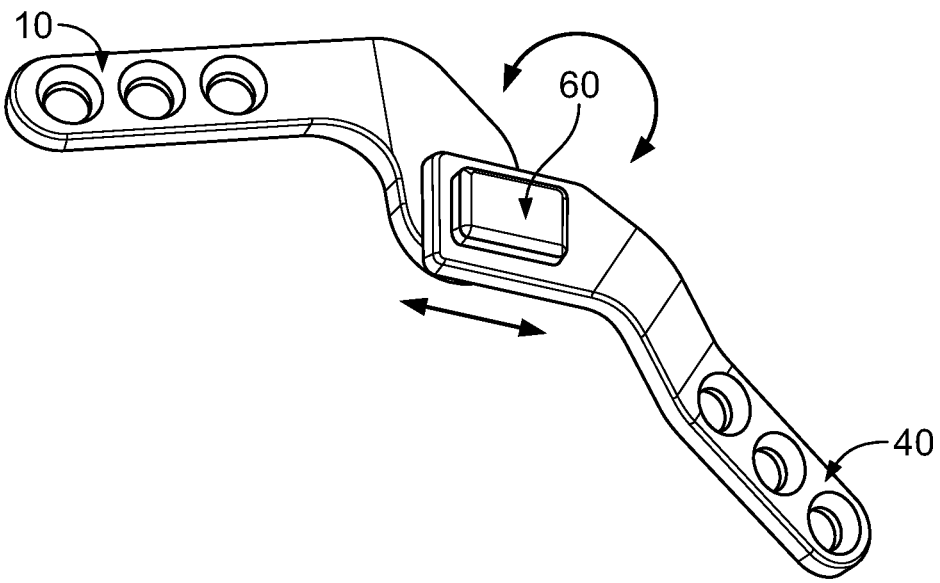
FIG. 1 is a perspective view of the apparatus of the present disclosure fully assembled, including the femoral component, the tibial component, and the articular sliding insert component.

A modular surgically implanted apparatus is disclosed that can be used in canine, feline, and other quadruped animal species (e.g., domestic or exotic) to stabilize an unstable quadruped stifle joint that may be due to any number of causes (e.g., soft tissue or hard tissue injury of the stifle ligaments, tendons and their attachments and surrounding structures). The modular device (e.g., canine internal stifle stabilizing system) can be surgically implanted on a temporary or permanent basis to provide veterinary orthopedic surgical stabilization of a stifle joint (e.g., quadruped stifle joint). The system stabilizes the unstable stifle joint during all phases of the stride and allows normal stifle flexion, extension, internal rotation, external rotation, joint compression and expansion, varus and valgus movement, while continuously impeding abnormal cranial tibial thrust during all phases of the stride. The system works for primary treatment (e.g., stabilize a quadruped stifle) for a partial or complete cranial cruciate ligament injury (e.g., rupture) or avulsion, a partial or complete caudal cruciate ligament injury (e.g., rupture) or avulsion, a partial or complete medial collateral ligament injury (e.g., rupture) or avulsion, a partial or complete lateral collateral ligament injury (e.g., rupture) or avulsion, a congenital or traumatic medial patellar luxation or avulsion, a congenital or traumatic lateral patellar luxation or avulsion, a congenital or traumatic patellar tendon avulsion, a patellar fracture, a traumatic fracture to either the distal femur or proximal tibia, or any combination thereof (e.g., all of the above).

A stifle stabilizing system is provided as a modular, stifle stabilizing device that can be permanently or temporarily surgically implanted and attached onto the medial side of the distal femur and proximal tibia of quadrupeds. The components of the system are interdependent and interconnected.

The system permits normal stifle joint movement in all planes, while continually providing support. All components of the stifle stabilizing system could be made of a biocompatible surgical material. The stabilizing device is centered over the medial aspect of the quadruped stifle joint.

The device includes a femoral component, a tibial component, and an articular sliding insert component. The tibial and femoral components are fastened to the medial aspect of the femur and tibia by a varying number of fasteners. The distal end of the femoral component contains a coupling member, which could be permanently attached to the femoral component. The coupling member provides multiple degrees of movement, while remaining completely captured, as explained in more detail below. Although the drawings depict the coupling member as a ball and stem, any other suitable coupling member could be used, such as 'T' and groove, disc and sleeve, etc. Further, the coupling member could be any shape that could fit into the slot of the articular sliding component and allow rotation and twisting between the femoral component and tibial component, such as any shape with a rounded type surface (e.g., oval, oblong, etc.).

The proximal tibial component has a rectangular space that accepts and holds the articular sliding insert component, such as by a pressure fit into the rectangular space provided on the proximal tibial component. The articular sliding insert component includes a groove (e.g., channel) that receives the ball to lock the femoral and tibial components together. The articular sliding insert component also includes a flange on the underside thereof. In operation, the flange is located between the femoral and tibial components and has a bevelled edge (e.g., a ten degree bevelled edge) on either side, allowing for (and limiting) maximum internal and external rotation of the stabilized stifle joint. The system permits normal stifle joint movement in all planes, while continually providing support.

When assembled and implanted in a patient, the articulation between the components of the stifle stabilizing system ensures that the implant allows, and does not impede, the normal range of motion, normal compression and expansion, normal valgus and varus movement and normal external and internal rotation of the quadruped stifle, while continuously stabilizing the stifle joint and thereby preventing abnormal tibial thrust in all phases of the stride. The system provides continuous support and stabilization (e.g., of a tibia relative to a femur) and allows for (and does not inhibit) the normal extension (e.g., about 160 degrees) and flexion (e.g., about 40 degrees) range of motion of the stifle joint (e.g., tibia in relation to the femur), during any phase (e.g., weight bearing and non-weight bearing) of the stride. In the canine patient, the angle of the stifle is measured from the lateral side, and is the angle formed by intersecting lines bisecting the centers of the femur and tibia. In the normal canine, the stifle range of motion is approximately from one hundred and sixty (160) degrees in full extension to approximately forty (40) degrees in full flexion.

The system of the present disclosure provides for normal internal (e.g., approximately 10 degrees) and external (e.g., approximately 10 degrees) tibial rotation. Tibial rotation is measured as the amount of inward or outward twisting of the tibia relative to the femur. The normal canine tibia has 10 degrees of valgus and varus movement relative to the femur.

Figure 2:
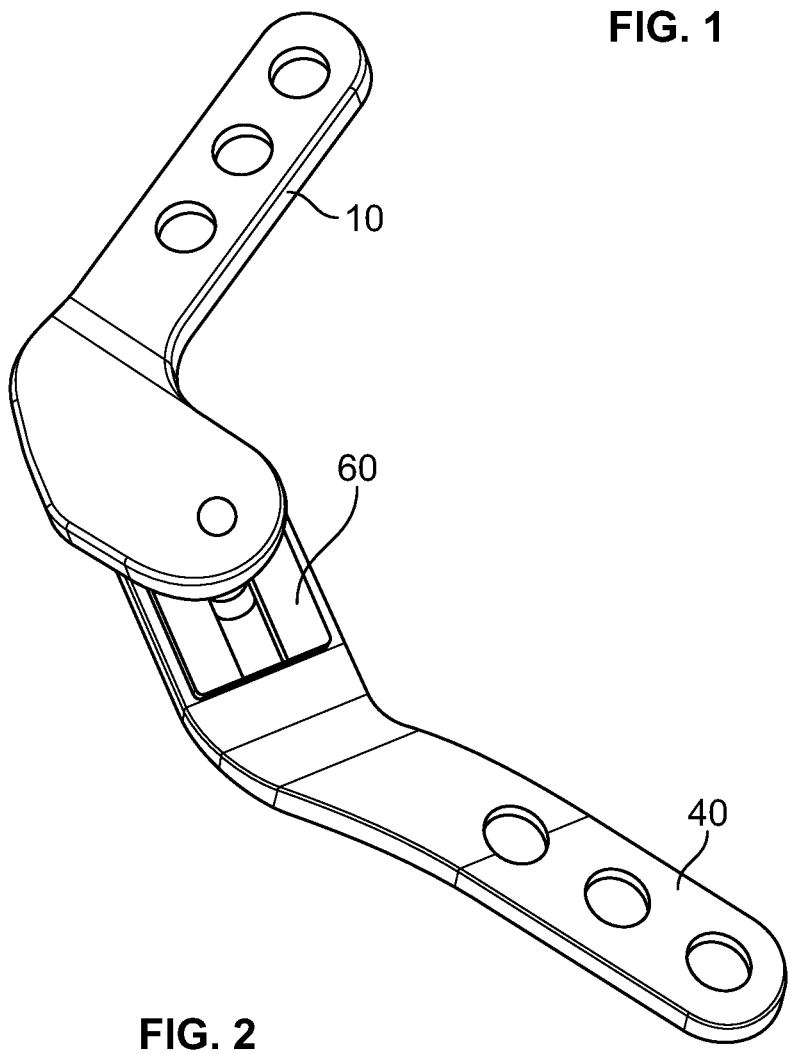
FIG. 2 is a bottom perspective view of the apparatus shown in FIG. 1.

FIG. 1 is a perspective view of the assembled system of the present disclosure, and FIG. 2 is a back perspective view of the system shown in FIG. 1. The system is a surgically implantable, modular stifle stabilizing device comprising a femoral component 10, a tibial component 40, and an articular sliding insert component 60. Each stabilizing component can be separately manufactured/machined and then interconnected. More specifically, the femoral component interconnects with the tibial component via the articular sliding insert component. These connections between the components allow the individual components to maintain the normal range of motion and normal external and internal rotation of the quadruped stifle (e.g., canine, feline, etc.), while continuously stabilizing the stifle joint. As indicated by the arrows, and as explained in further detail below, the femoral component 10 translates along the channel of the articular sliding insert component 60, and the tibial component 40 rotates about the ball of the femoral component 10.

Figure 3A:
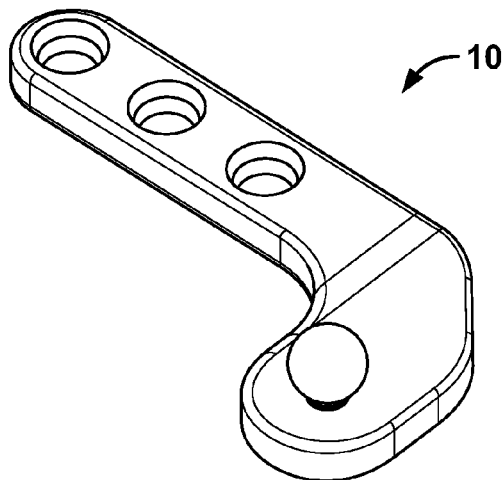
FIGS. 3A-3E are perspective, front, back, side, and exploded perspective views, respectively, of the femoral component.
Figure 3B:
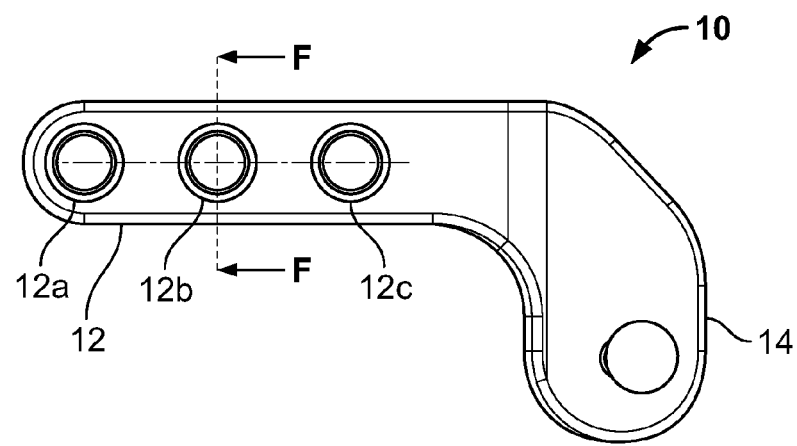
Figure 3C:
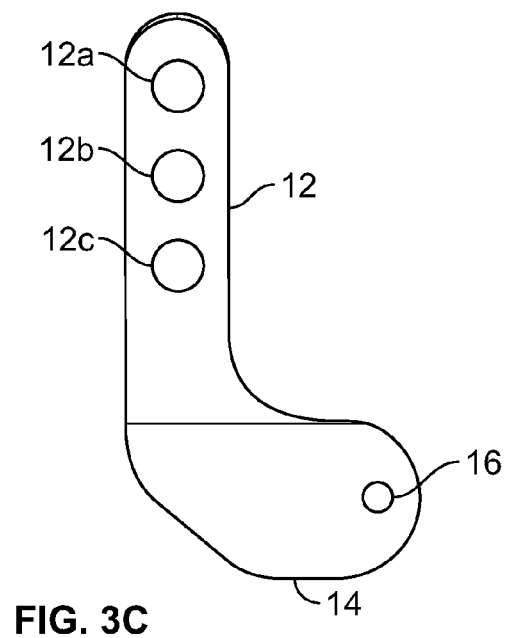

FIGS. 3A-3E are perspective, front, back, side, and exploded perspective views, respectively, of the femoral component 10. FIG. 3F is a cross-section view taken along line F-F in FIG. 3B, and FIG. 3G is a cross-section view taken along line G-G in FIG. 3D. As shown in FIG. 3A-3C, the femoral component 10 is a form fitting (e.g., precontoured and contourable), hockey stick shaped, curved component that conforms, and can be permanently or temporarily attached, to the contour of a femur (e.g., the medial side of the distal third of the femur, medial aspect of the distal femoral diaphysis, etc.).

The femoral component 10 can be made from a number of acceptable, biocompatible, implantable materials (e.g., 316MVL stainless steel, titanium, Ultra High Molecular Weight Polyethelene (UHMWPE), etc.). Exposed edges of the femoral component 10 can be rounded and smooth. The dimensions of the femoral component 10 can vary, such as according to the size of the patient (e.g., based wholly or in part on the body weight of the patient). More specifically, the length, width, and/or thickness of the femoral component 10 can vary with the size of patient (e.g., approximately 25-85 mm in length, approximately 5-45 mm in width, and about 2-3 mm in thickness).

The femoral component 10 includes a leg portion 12 and a bottom portion 14, which form plane angles with respect to one another (e.g., the general "L" shape) and also form dihedral angles with respect to one another. The leg portion 12 can have front and back generally planar faces and opposing, generally planar edges. At the distal end, the edges can terminate in a rounded distal edge. The bottom portion 14 includes front and back generally planar faces and an edge that defines a bulbous shape.

The femoral component 10 contains attachment holes in leg portion 12 and an aperture 16 in bottom portion 14. Any number of attachment holes 12a, 12b, and 12c could be used (e.g., two (2) to three (3) permanent attachment holes). These holes 12a, 12b, and 12c can be aligned and extend through the front and back generally planar faces. The diameter of these holes can vary such that they will accept the appropriate sized screw, or other fastener (e.g., 3.5 mm diameter holes for placement of a 3.5 mm cortical bone screw). The holes 12a, 12b and 12c can be sized to have a sufficient diameter such that the head of the screw (e.g., a 3.5 mm cortical screw), fits flush with the femoral component 10. Any sized bone screws could be used (e.g., 2.0 mm, 2.7 mm, or 3.5 mm cortical bone screws), and the holes 12a, 12b, and 12c could be sized accordingly. Further, the femoral component 10 could utilize locking technology (e.g., locking screws and locking attachment holes 12a, 12b, and 12c).

As shown in FIGS. 3A-3E, a ball 20 and stem 22 are located on the bottom portion 14 of the femoral component 10. The stem 22 is received by aperture 16, and the ball 20 extends outward from the outer surface of the bottom portion 14 of the femoral component 10 at approximately 90 degrees. The ball 20 and stem 22 can be formed separately and joined together or they can be of a unitary construction. The stem 22 can be pressure fit into an aperture 16 in the bottom portion 14, although any suitable attachment method could be used (e.g., aperture 16 and stem 22 could be threadably engaged with one another, a series of laser welds could be used, etc.). The shape of the ball 20 can be varied as desired provided it can interlocked with the tibial component 40, such as by way of insert component, as will be described below in more detail. The ball 20 provides the stifle joint with continuous support against abnormal tibial thrust during both full extension and full flexion from approximately one hundred and sixty (160) degrees (full extension) to approximately forty (40) degrees (full flexion). The ball 20 and stem 22 form the articulation point for the femoral component 10.

Figure 3D:
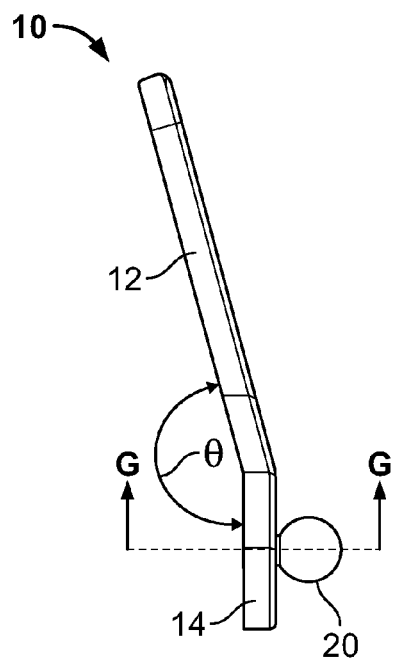
Figure 3E:
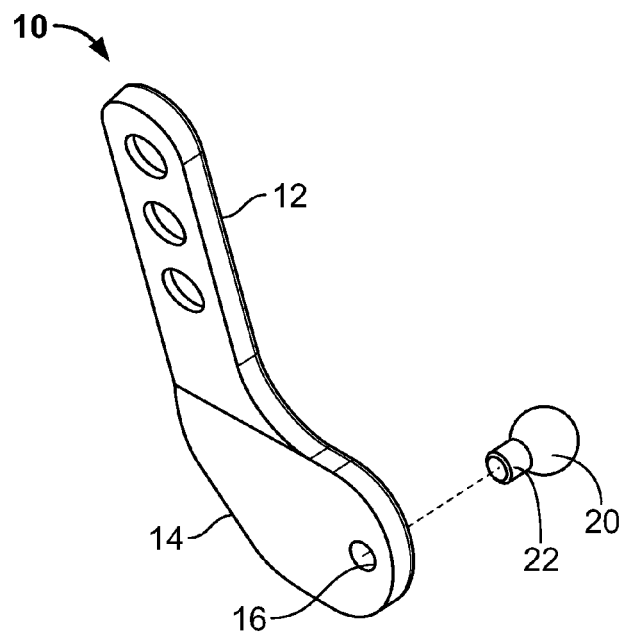
Figure 3F:
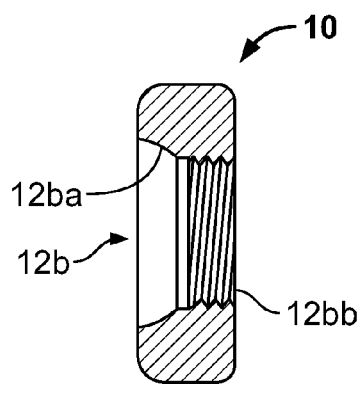
FIG. 3F is a cross-section view taken along line F-F in FIG. 3B.
Figure 3G:
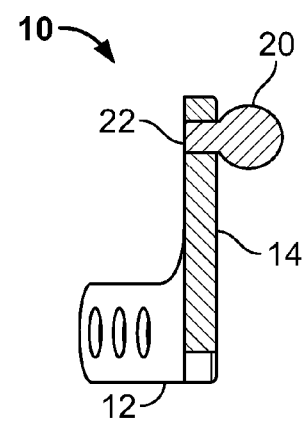
FIG. 3G is a cross-section view taken along line G-G in FIG. 3D.

As shown in FIG. 3D, the bottom portion 14 can be positioned at an angle ⊖ (e.g., dihedral angle) with respect to leg portion 12. The distal end of the femoral component 10 can be contoured to the shape of the femoral condyle and could be designed to be elevated away (e.g., 1-2 mm) from the bone of the distal femur (e.g., dihedral angle) so as not to impede femoral soft tissues.

FIG. 3F is a cross-sectional view taken along line F-F on FIG. 3B showing an aperture 12B that could be partially threaded at one area 12BB while having a unthreaded recessed area 12BA. Any suitably configured aperture could be used in the femoral or tibial component. FIG. 3G is a cross-sectional view taken along line G-G on FIG. 3D showing the insertion of the ball 20 and stem 22 discussed in more detail below.

Figure 4A:
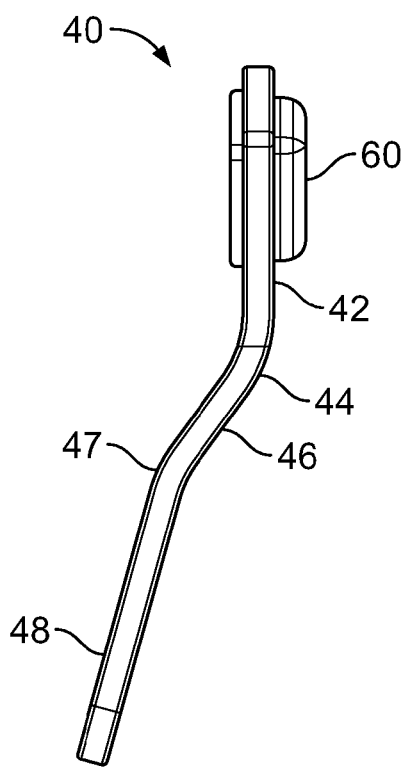
FIGS. 4A-4C are side, front, and perspective views, respectively, of the tibial component and the articular sliding insert component.
Figure 4B:
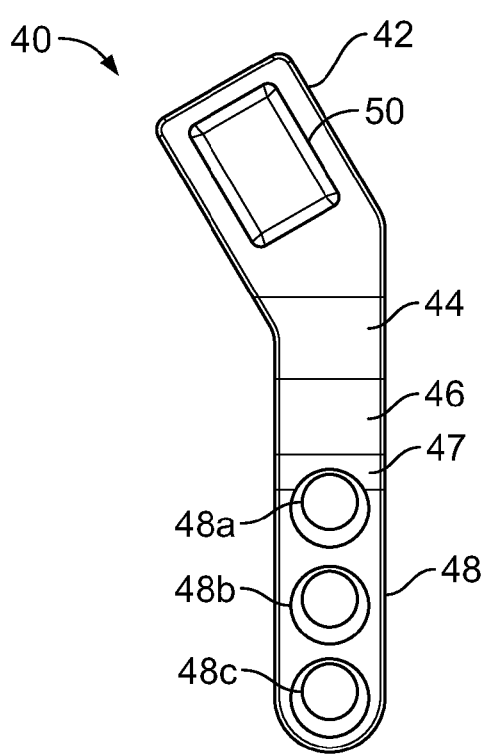
Figure 4C:
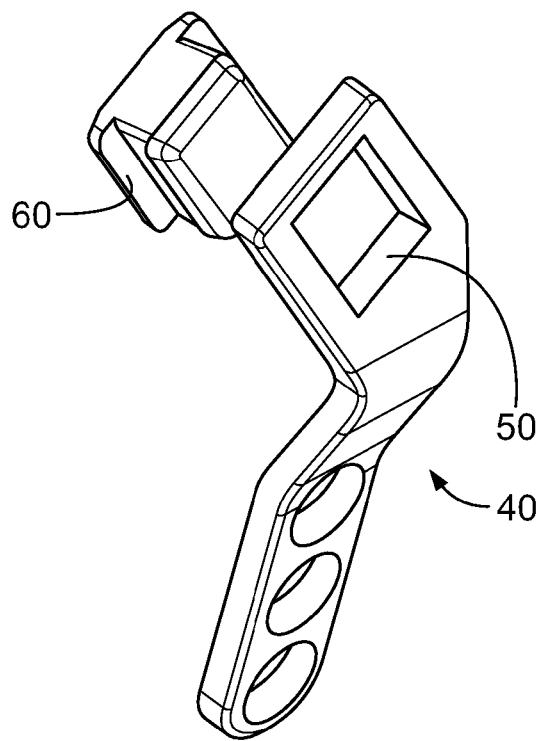

FIGS. 4A-4C are side, front, and perspective views, respectively, of the tibial component 40 and the articular sliding insert component 60. The tibial component 40 conforms to the contours of a tibia (e.g., proximal medial tibia). The tibial component 40 can be made from a number of acceptable, biocompatible, implantable materials (e.g., 316MVL stainless steel, titanium, UHMWPE, etc.). Exposed edges of the tibial component 40 can be rounded and smooth. The length, width, and thickness of the tibial component 40 can vary with the size of patient (e.g., approximately 25-85 mm in length, approximately 5-45 mm in width, and about 2-3 mm in thickness).

As shown in the side view of FIG. 4A, the tibial component 40 could be curved. More specifically, the tibial component 40 could have a first proximal planar portion 42, a first bend 44, a second central planar portion 46, a second bend 47 (e.g., the second bend 47 opposite in direction to the first bend 44), and a third distal planar portion 48. The first, second, and third planar portions 42, 46, and 48 include front and back general planar faces and opposing generally planar edges. At the distal edge, the edges terminate in a rounded distal edge.

The third distal planar portion 48 of the tibial component 40 contains attachment holes 48a, 48b and 48c for attachment to the tibia (e.g., two to three permanent attachment holes). The diameter of these holes can be sized such that they will accept the appropriate sized screw, or other fastener (e.g., 3.5 mm in diameter for placement of a 3.5 mm cortical bone screw). The holes 48a, 48b and 48c can be sized to have a sufficient diameter such that the head of the screw (e.g., 3.5 mm cortical bone screw), will fit flush with the tibial component 40. Any sized bone screws could be used (e.g., 2.0 mm, 2.7 mm, or 3.5 mm), and the holes 48a, 48b and 48c can be sized accordingly. The attachment holes can be sized such that they will accept the appropriate sized screw and so that the screw is flush when implanted. Further, the tibial component 40 could utilize locking technology (e.g., locking screws and locking attachment holes 48a, 48b and 48c).

The first planar portion 42 forms a dihedral angle (e.g., bend 44) with the second planar portion 46, and the second planar portion 46 forms a dihedral angle (e.g., bend 47) with the third planar portion 48. The proximal part of the tibial component 40, when implanted, can be elevated (e.g., about 1-2 mm) off the medial surface of the proximal tibia (e.g., dihedral angles) to allow for the clearance of the soft tissues of the proximal stifle. The first proximal planar portion 42 of the tibial component 40 has wider edge to edge front and back generally planar faces compared with the second planar portion 46 and third planar portion 48.

As shown in FIG. 4B, the first planar portion 42 could be angled (e.g., plane angle) with respect to the second planar portion 46, whereas the second and third planar portions 46 and 48 could be aligned. Additionally, the first proximal planar portion 42 includes a slot 50 (e.g., rectangular) extending through the front and back generally planar faces. This rectangular slot 50 on the tibial component 40 receives, such as by a pressure fit attachment, the articular sliding insert component 60. The rectangular slot 50 allows the articular sliding insert component 60 to be firmly held in place. However, any other suitable way of connecting the insert component 60 to the tibia component 40 and the femoral component 10 to the insert component 60 could be used.

FIGS. 5A-5E are perspective, top, front, side, and bottom views, respectively, of the articular sliding insert component. The articular sliding insert component 60 could be rectangular shaped, and conforms to (and pressure fits into) the slot 50 (e.g., rectangular) of the tibial component 40. The articular sliding insert component 60 allows for the internal and external rotation at any phase of extension or flexion. The articular sliding insert component 60 could be rectangular and be made of a biocompatible, surgically implantable material that preferably has good wear characteristics, is inert and carries a low coefficient of friction. As such, the insert component could be made of a plastic such as a UHMWPE material.

The articular sliding insert component 60 (e.g., intermediate component) comprises a rectangular-shaped component that conforms to, and is received by, the rectangular opening 50 of the proximal tibial component 40, discussed in FIGS. 4A-4C above. However, the opening 50 and the insert component 60 could be of any suitable shape. The articular sliding insert component 60 has a top 62, side walls 64, and rear wall 69 surrounding a central channel 67 (e.g., circular), a front wall 68, as well as lower angled flange extensions 66 extending outwardly from the lower portion of sidewalls 64, and upper shoulder extensions 63. More specifically, the underside of the articular sliding insert component 60 has an angled/bevelled flange 66 extending outward.

The insert component 60 could be inserted in slot 50 of tibial component 40, and then secured therein by shoulders 63, and flanges 66. The insert 60 could be secured in the tibial component 40 by a pressure fit or otherwise. When assembled, the insert component 60 can be maintained in position with respect to the tibial component by virtue of the tibial component fitting between the lower flanges 66 of the insert component 60 and corresponding shoulders 63 positioned in facing relationship thereto. The flanges 66 could be level with the edge of the tibial component 40. The flanges 66 provide continual separation of both the tibial and femoral components. This extension can be angled/bevelled to allow and limit internal and external rotation (e.g., ten degrees) of the tibial component 40 relative to the femoral component 10. The relative rotation could be limited to approximately ten (10) degrees of internal rotation and ten (10) degrees of external rotation by the angled flanges 66.

Figure 5A:
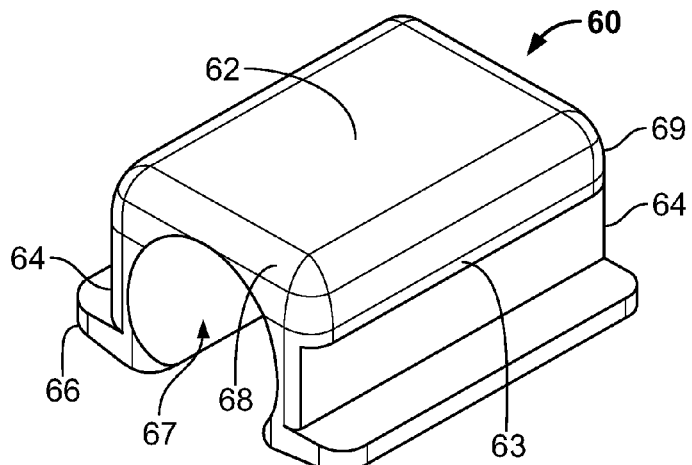
FIGS. 5A-5E are perspective, top, front, side, and bottom views, respectively, of the articular sliding insert component.
Figure 5B:
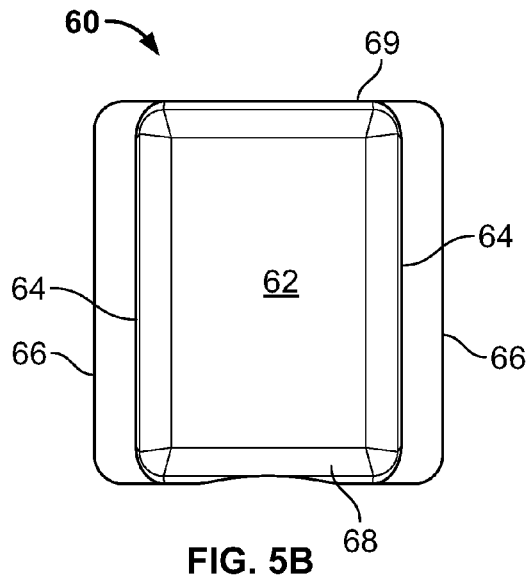
Figure 5C:
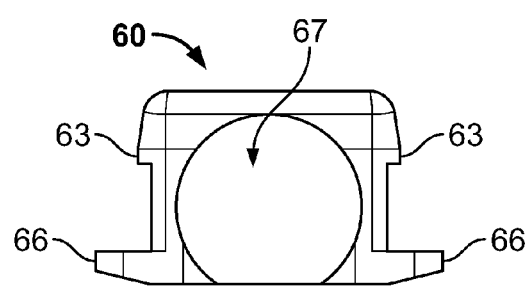
Figure 5D:
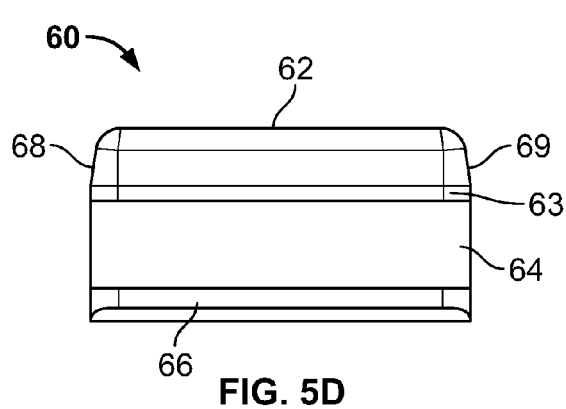
Figure 5E:
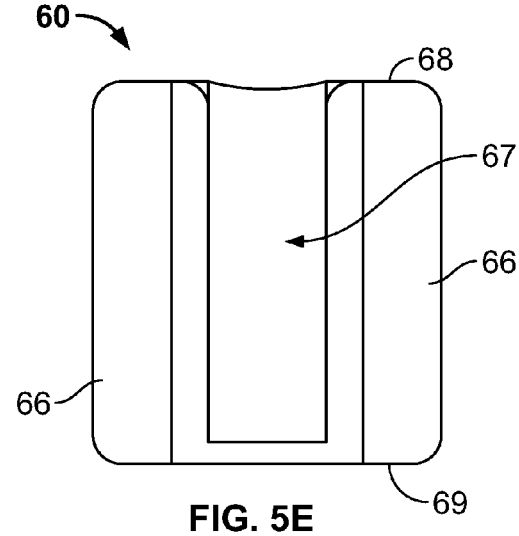

As shown in FIG. 5C, the central channel 67 (e.g., cavity) is cylindrically shaped, and could extend through one or both of the forward and rear walls 68 and 69. Further, the channel could extend through the bottom of the insert component 60 thereby providing enough room to provide lateral movement for the stem 22, but insufficient room for the ball 20 to detach from the insert component 60. The channel 67 could extend through the forward side 68 for at least a portion toward the rear wall 69. In other words, one end of the insert 60 could have a rear wall 69 that closes one end of the channel 67 (or the channel could extend through the rear wall 69).

The articular central channel 67 of sliding insert component 60 is configured to accept and interlock (e.g., correspond in size and shape) with the spherical ball 20 attached to the femoral component 10, discussed in FIGS. 3A-3G above. As such, the connection between the cylindrical channel 67 and the ball 20 creates a ball and socket type joint that allows for rotational and pivotal/swivel movement of the ball 20 with respect to the channel 67, and accordingly, allows for such movement of the femur with respect to the insert component 60 and the tibial component. Further, the channel 67 allows for the ball to slide from the forward end 68 to the rear end 69 (e.g., along the length of the channel) thereby providing for additional translational movement of the ball 20 with respect to the channel 67, and accordingly, allows for such movement of the femoral component with respect to the insert component 60 and the tibial component. The ball 20 is able to rotate within and slide along the channel 67 after implantation permitting normal joint movement but preventing abnormal tibial thrust. This allows the femoral ball 20 to be captured and held in place during all phases of the stride. When the insert 60 is attached to the tibial component, the slot 50 could close off one (or both) ends of the cavity 67 to prevent the ball from escaping the cavity 67.

Figure 6A:
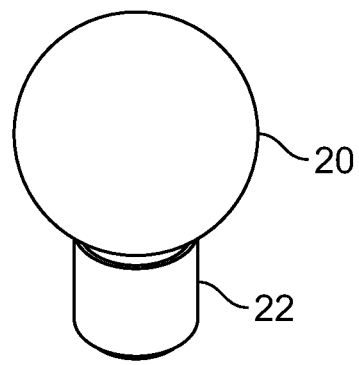
FIGS. 6A-6C are perspective, side, and bottom views, respectively, of the femoral coupling member of the apparatus.
Figure 6B:
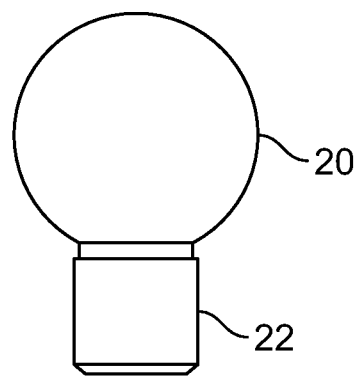
Figure 6C:
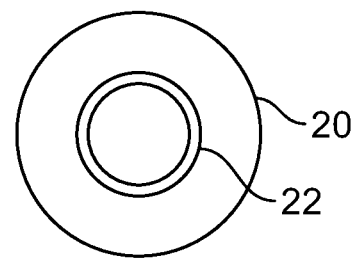

FIGS. 6A-6C show views of the ball 20 and stem 22 that connects with the femoral component 10 and the articular sliding component 60, as discussed above. Like the femoral and tibial components, the ball 20 and stem 22 can be made of a biocompatible material. The ball 20 engages the articular sliding insert component 60, described in FIGS. 5A-5E above, which is in turn inserted into the tibial component. This forms the articulation point on the femoral component.

Figure 7:
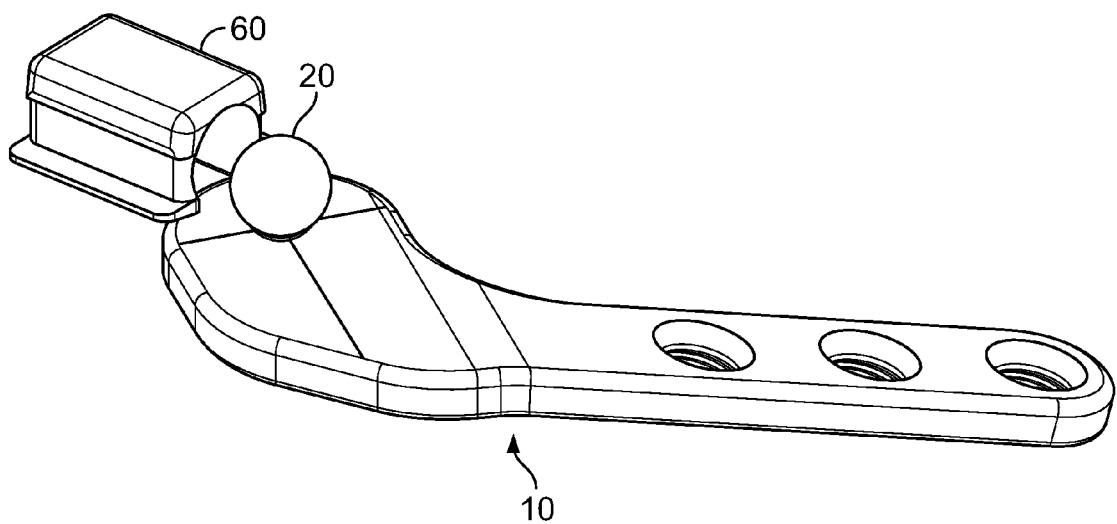
FIG. 7 is a perspective view of the articular sliding insert component positioned to receive the femoral ball attached to the femoral component.
Figure 8:
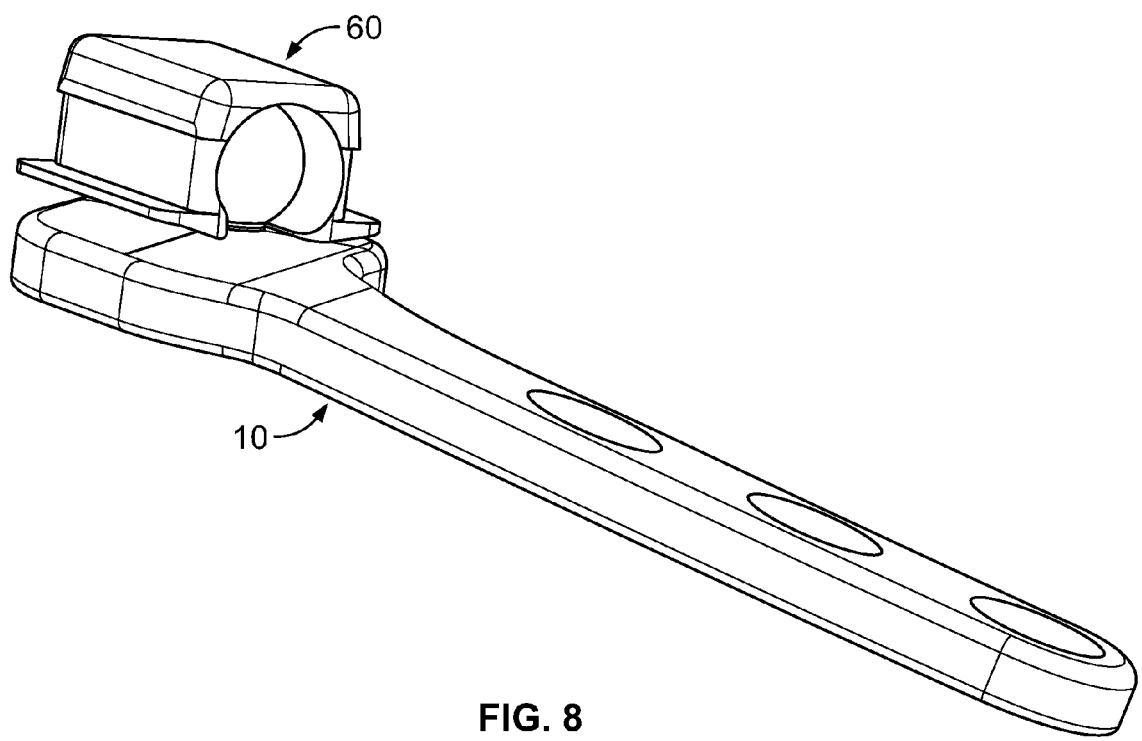
FIG. 8 is a perspective view of the femoral ball positioned in the articular sliding insert component.
Figure 9:
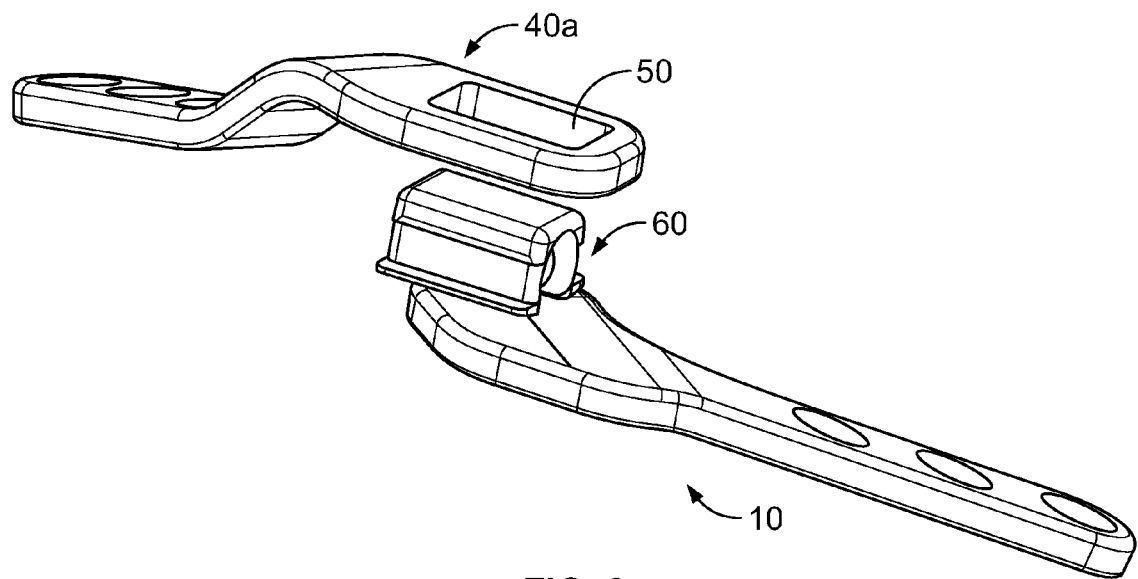
FIG. 9 is a perspective view of the tibial component positioned to receive the articular sliding insert component.
Figure 10:
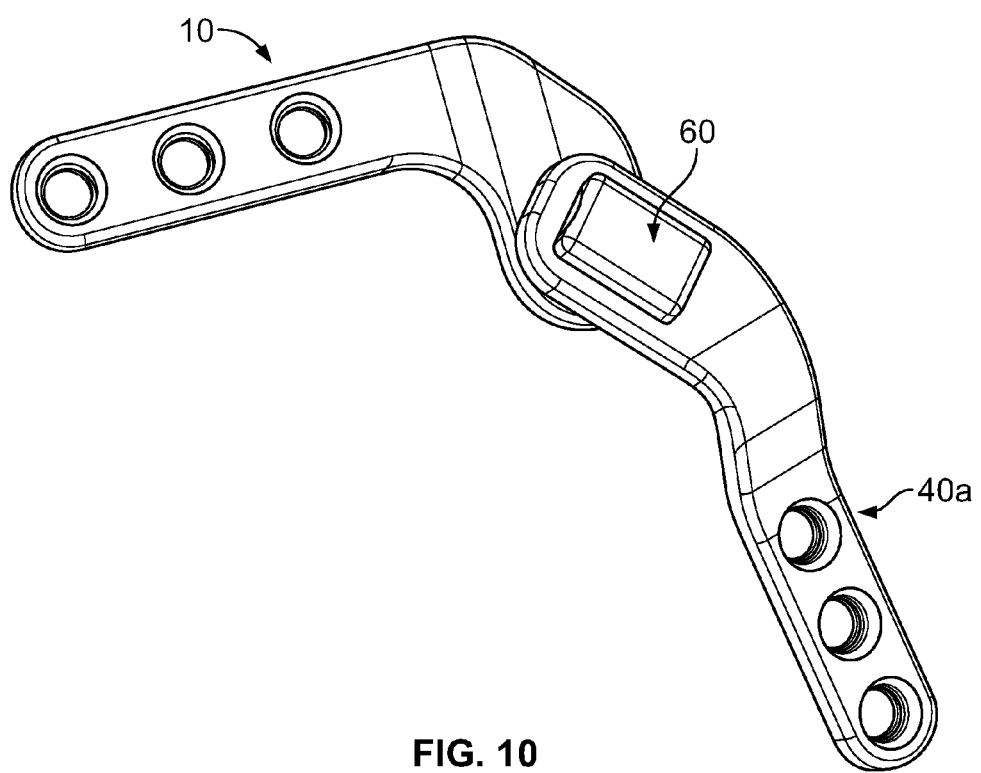
FIG. 10 is a perspective view of another aspect of a fully assembled apparatus.

FIGS. 7-10 are perspective views showing the assembly of the system. FIG. 7 is a perspective view showing the insert component 60 positioned to slide over and engage with ball 20 attached to femoral component 10. FIG. 8 is a perspective view showing the ball 20 attached to the femoral component 10 engaged within the insert component 60. FIG. 9 is a perspective view of the tibial component 40a positioned to receive the insert component 60 into rectangular slot 50. Tibial component 40a is like tibial component 40 of FIGS. 4A-4C, but with rounded corners. FIG. 10 is a perspective view showing the fully engaged device.

Figure 11:
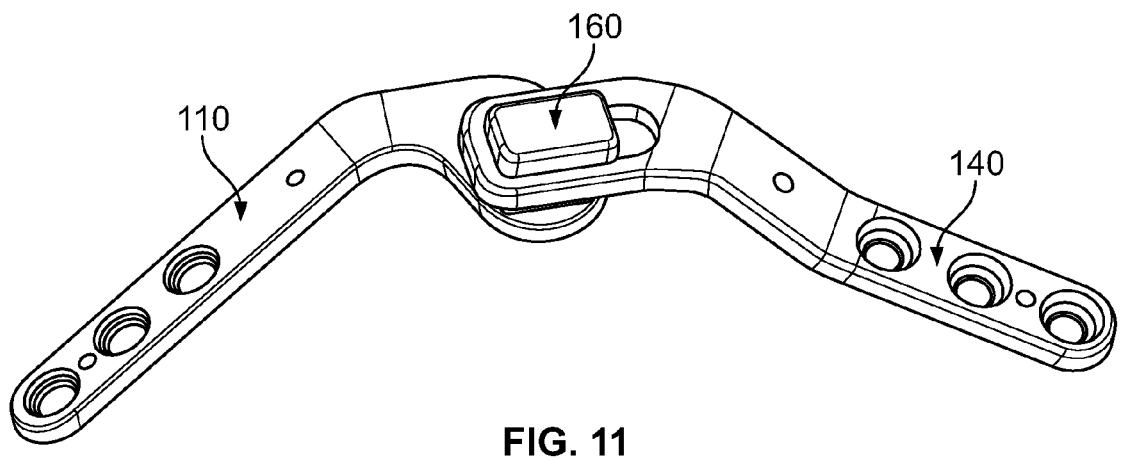
FIG. 11 is a perspective view of another aspect of the apparatus fully assembled.
Figure 12:
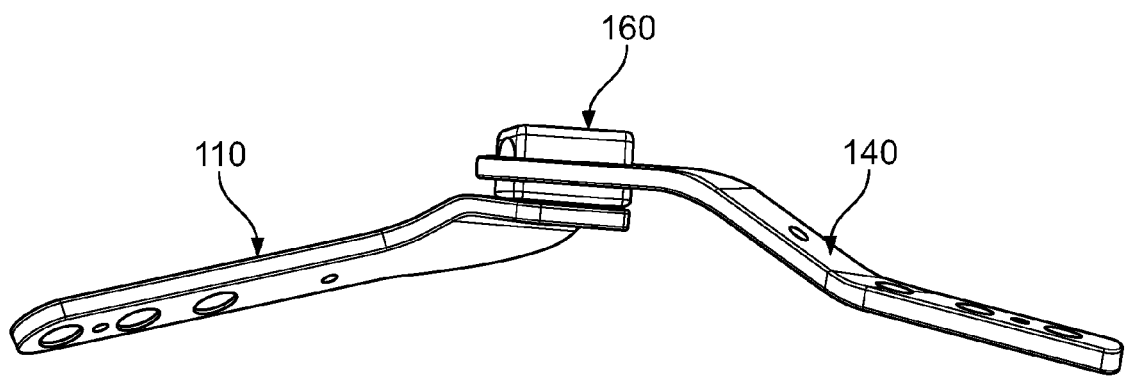
FIG. 12 is a side view of the apparatus shown in FIG. 11.

FIG. 11 is a perspective view of another aspect of the assembled system, and FIG. 12 is a side view of the apparatus of FIG. 11 fully assembled. As with the aspect described above, the system includes a femoral component 110, a tibial component 140, and an articular sliding insert component 160. The system shown in FIG. 11 is configured and functions in the same manner as the system shown in FIGS. 1-10 except as discussed, and like elements are given like reference numerals, plus 100.

Figure 13A:
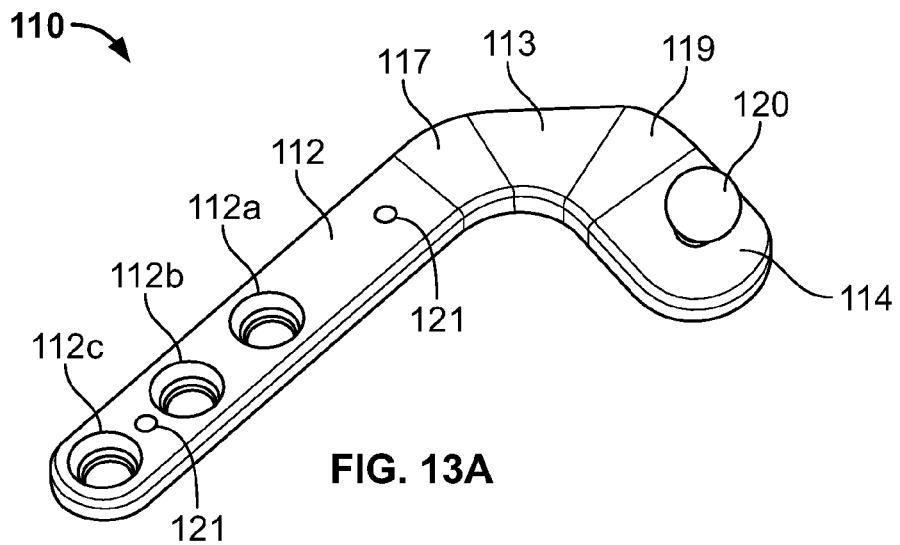
FIGS. 13A-13C are perspective, rear, and side views of the femoral component shown in FIG. 11.
Figure 13B:
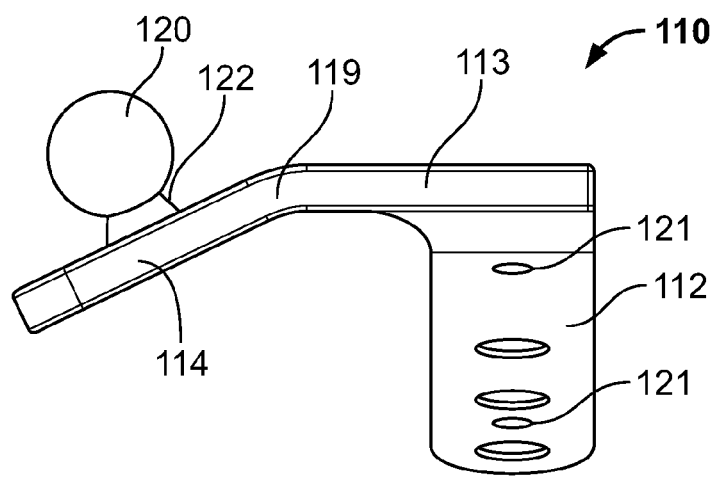
Figure 13C:
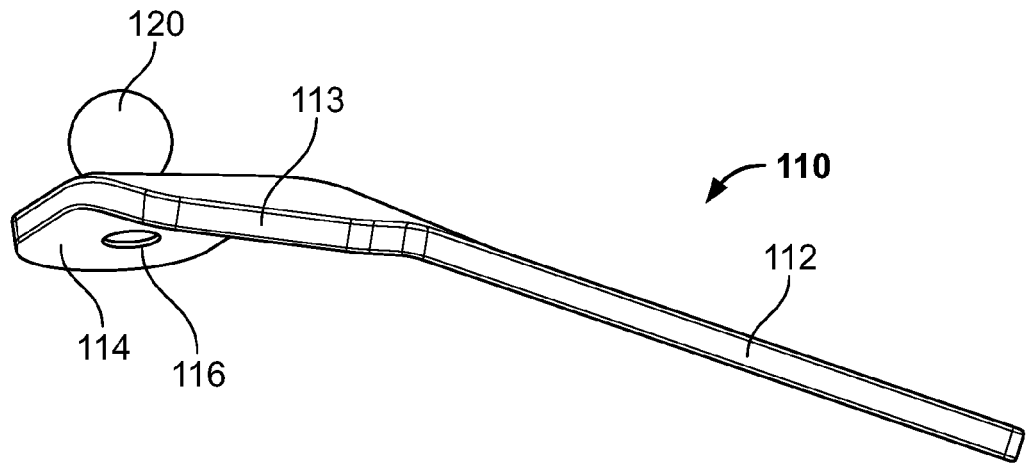

FIGS. 13A-13C are perspective, rear, and side views of the femoral component 110 of FIG. 11. Similar to the femoral component shown in FIGS. 3A-2G, femoral component 110 includes a leg portion 112 and a bottom portion 114, but also includes an intermediate portion 113. The leg portion 112 and bottom portion 114 each form plane angles (e.g., in the same direction) with respect to the intermediate portion 113 therebetween, thereby forming a general hockey stick shape. The femoral component 110 could have a dihedral angle (e.g., first bend 117) between the leg portion 112 and intermediate portion 113, and a dihedral angle (e.g., second bend 119) between the intermediate portion 113 and the bottom portion 114. The first bend 117 and second bend 119 being in the same direction.

The femoral component 110 contains attachment holes 112a, 112b, and 112c in leg 112 and an aperture in bottom portion 114. The femoral component 110 could further comprise a ball 120 and stem 122 in bottom portion 114 of the femoral component 110. The stem 122 is received by aperture 116, and the ball 120 extends outward from the outer surface of the bottom portion 114 of the femoral component 110 at approximately 90 degrees. The femoral component 110 further comprises one or more temporary attachment holes 121, which could vary in number and location. The temporary attachment holes 121 could be used for temporary fixation with a surgical tool or temporary surgical implant (e.g., holding pins, k-wire, etc.). As shown, one of the temporary attachment holes 121 is located between attachment hole 112b and attachment hole 112c. Alternatively, the temporary attachment hole 121 could be located at an end of the leg 112 (proximate attachment hole 112c, but not proximate attachment hole 112b). Further, there could be a temporary attachment hole proximate the stem 122. Further, the femoral component 110 could utilize locking technology (e.g., locking screws and locking attachment holes 112a, 112b and 112c).

Figure 14:
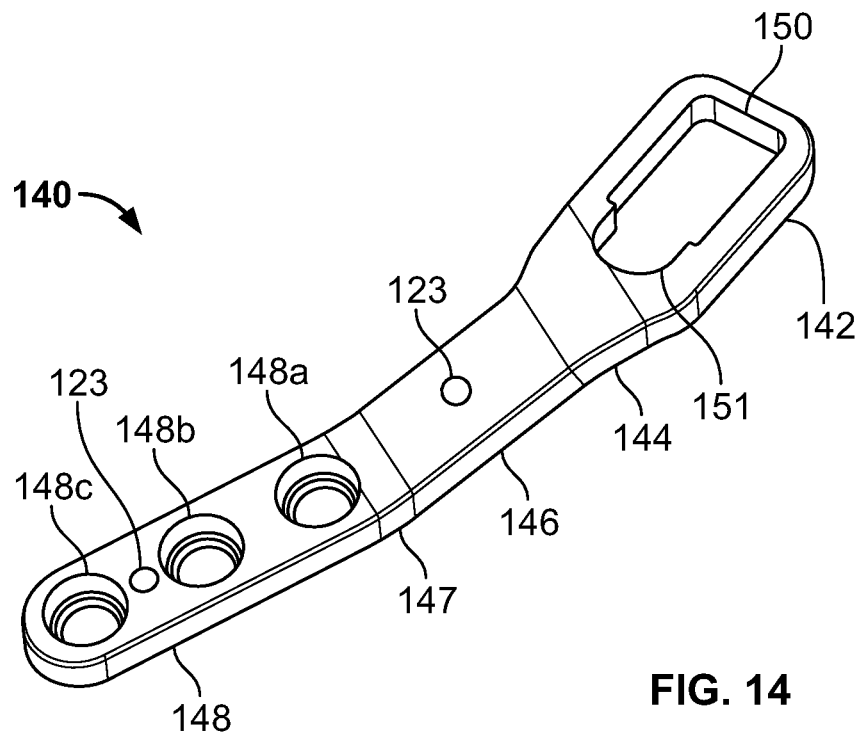
FIG. 14 is a perspective view of the tibial component shown in FIG. 11.

FIG. 14 is a perspective view of the tibial component 140 of FIG. 11. The tibial component 140 could have a first proximal planar portion 142, a first bend 144, a second central planar portion 146, a second bend 147 (e.g., the bend opposite in direction to the first bend), and a third distal planar portion 148. The first, second, and third planar portions 142, 146, and 148 include front and back general planar faces and opposing generally planar edges. The third distal planar portion 148 of the tibial component 140 contains attachment holes 148a, 148b and 148c for attachment to the tibia (e.g., two to three permanent holes). The tibial component 140 further comprises one or more temporary attachment holes 123. The temporary attachment holes 123 could be used for temporary fixation with a surgical tool or temporary surgical implant (e.g., holding pins, k-wire, etc.). As shown, one of the temporary attachment holes 123 is located between attachment hole 148b and attachment hole 148c. Alternatively, the temporary attachment hole 123 could be located at an end of the third distal planar portion 148 (proximate attachment hole 148c, but not proximate attachment hole 148b). Further, the tibial component 140 could utilize locking technology (e.g., locking screws and locking attachment holes 148a, 148b and 148c).

The first proximal planar portion 142 could be angled (e.g., plane angle) with respect to the second proximal planar portion 146, whereas the second and third proximal planar portions 146 and 148 could be aligned. The first planar portion 142 forms a dihedral angle (e.g., bend 144) with the second planar portion 146, and the second planar portion 146 forms a dihedral angle (e.g., bend 147) with the third planar portion 148.

The first proximal planar portion 142 includes a slot 150 (e.g., rectangular) extending through the front and back generally planar faces. This rectangular slot 150 on the tibial component 140 receives, such as by a pressure fit attachment, the articular sliding insert component 160. The rectangular slot 150 allows the articular sliding insert component 160 to be firmly held in place. The slot 150 further includes a niche 151 (e.g., keyhole) at a distal end of the slot 150 of general corresponding shape and size to ball 120 of femoral component 110. The niche 151 allows the articular sliding component 160 to be inserted (e.g., pressure fit) into the slot 150 of the tibial component 140 prior to attachment of the ball 120 of the femoral component 110. In this way, the niche 151 allows the ball 120 of the femoral component 110 to engage the channel of the articular sliding insert component 160 when fixed in place in the tibial component 140, thereby allowing the ball 120 to be captured and held in place during all phases of the stride. This allows for greater flexibility in assembling the system.

Figure 15:
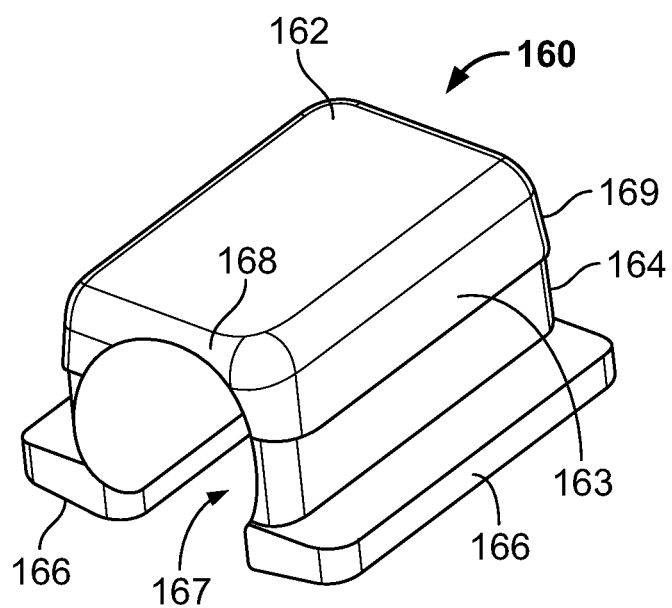
FIG. 15 is a perspective view of the articular sliding insert component shown in FIG. 11.

FIG. 15 is a perspective view of the articular sliding insert component 160 of FIG. 11. The articular sliding insert component 160 comprises a rectangular-shaped component that conforms to, and is received by, the rectangular opening 150 of the proximal tibial component 140, discussed in FIGS. 3A-3C and 21 above. The articular sliding insert component 160 has a top 162, side walls 164, and rear wall 169 surrounding a central channel (e.g., circular), a front wall 168, as well as lower angled flange extensions 166 extending outwardly from the lower portion of sidewalls 164, and upper shoulder extensions 163.

The insert component 160 could be inserted in slot 150 of tibial component 140, and then secured therein by shoulders 163, and flanges 166. The central channel 167 is cylindrically shaped, and could extend through one or both of the forward and rear walls 168 and 169. Further, the channel could extend through the bottom of the insert component 160 thereby providing enough room to provide lateral movement for the stem 122, but insufficient room for the ball 120 to detach from the insert component 160. The channel 167 could extend through the forward side 168 for at least a portion toward the rear wall 169. In other words, one end of the insert 160 could have a rear wall 169 that closes one end of the cavity 167 (or the channel could extend through the rear wall 169).

The components of the apparatus, such as the femoral and tibial components, or plates, can be either machined from a solid piece of material or they can be stamped using a stamping tool and then finished with machining operations, as is known in the art. Similarly, the insert component can be created by molding and/or machining.

While the components of the apparatus could be sold separately and assembled by a user such as a surgeon, the apparatus will generally be sold preassembled as a unit. The preassembled apparatus will be installed in an animal by attaching the femoral plate and tibial plate, respectively, to the femur and tibia of an animal.

Figure 16:
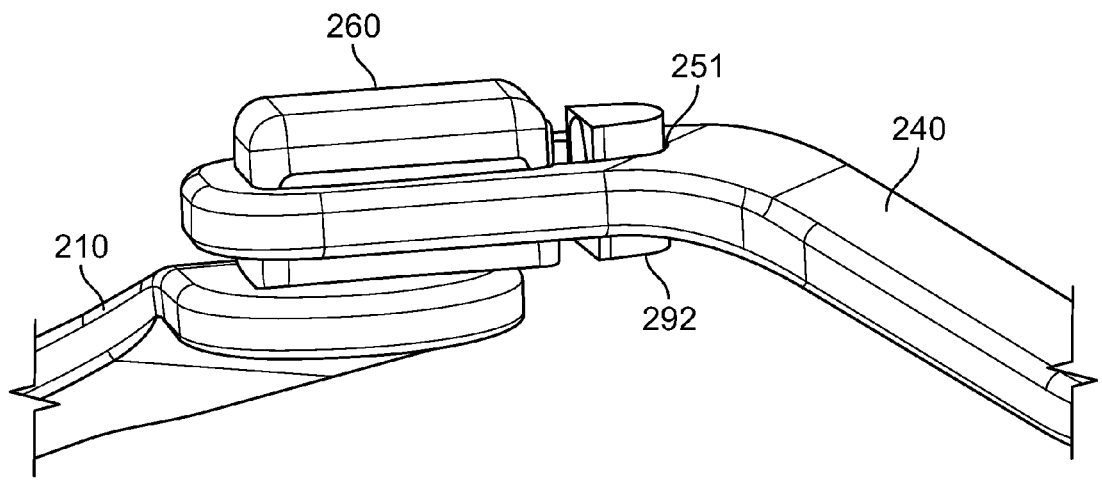
FIGS. 16-17 are partial perspective views of another aspect of the apparatus fully assembled.
Figure 17:
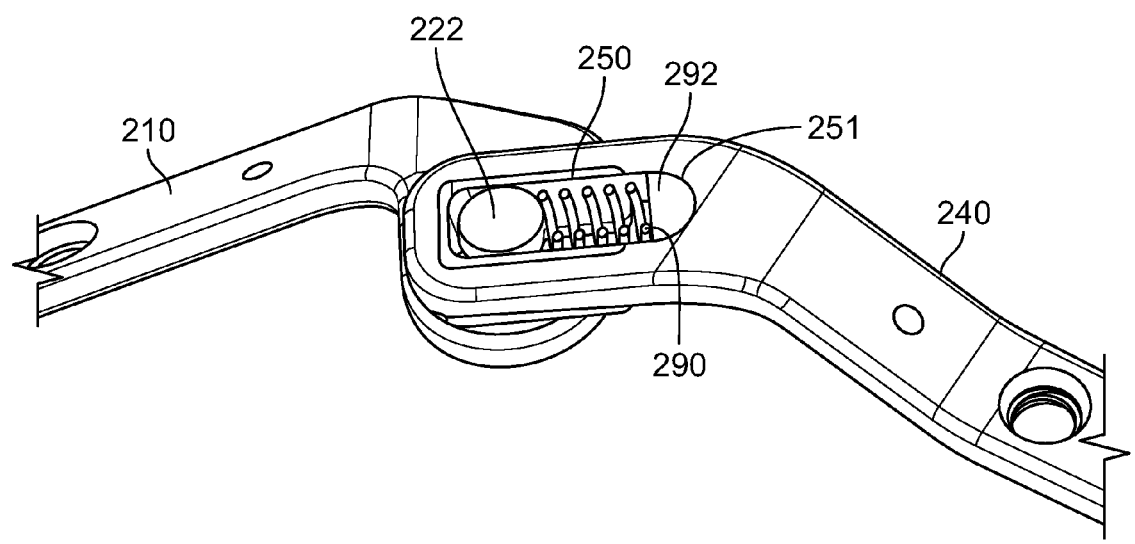

FIGS. 16-17 are partial perspective views of another aspect of the apparatus fully assembled. As with the aspect described above, the system includes a femoral component 210, a tibial component 240, and an articular sliding insert component 260. The system shown in FIGS. 16-17 are configured and function in the same manner as the system shown in FIGS. 1-15 except as discussed, and like elements are given like reference numerals, plus 100.

Chronic stifle instability can lead to debilitating end stage stifle disease. This disease process is characterized by severe joint thickening and loss of articular cartilage with bone on bone contact, which occurs primarily in the medial compartment of the quadruped stifle. The stifle stabilization system of the present disclosure could further include a weight reduction spring 290 to reduce the weight placed on the medial compartment of the quadruped stifle and thereby reducing the pain associated with end stage stifle disease. The spring 290 (e.g., compression spring) could be inserted into the sliding articulation channel 250 after the tibial component 240 has interconnected with the femoral component 210. The spring can be held in place with a spring retaining device 292 (e.g., locking button). The spring retaining device 292 could be assembled in the niche 251 of the slot 250 of the tibial component 240 (and could extend above and below the surface of the tibial component 240.

FIG. 17 is a partial view of FIG. 16 with the articular sliding component 260 removed. In this way, the spring 290 is located between a stem 222 of the femoral component 210 and the spring retaining device 292 of the tibial component 240. The spring 290 could come in a variety of strengths correlating to the size of the quadruped.

FIGS. 18-21B show another aspect of a stabilization system. The system shown in FIGS. 18-21B is configured and functions in the same manner as the system shown in FIGS. 1-15, except as discussed, and like elements are given like reference numerals, plus 200 (300).

Figure 18:
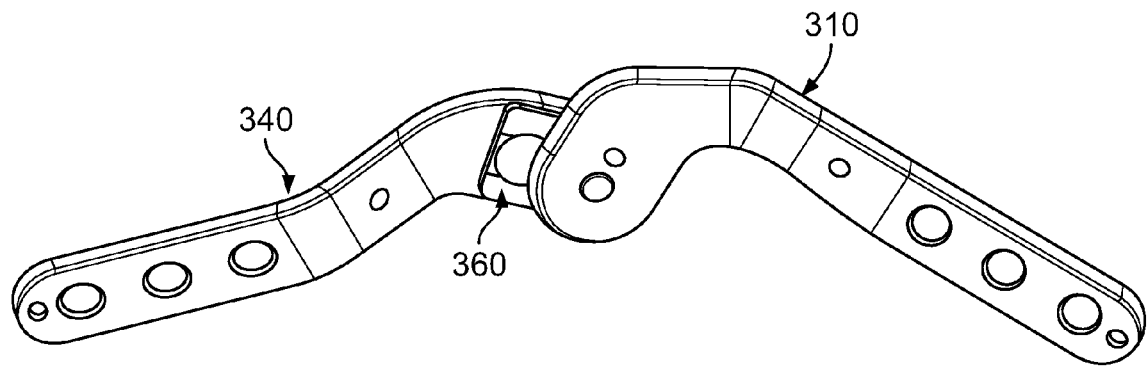
FIG. 18 is a perspective view of another aspect of an assembled stabilization system.
Figure 19:
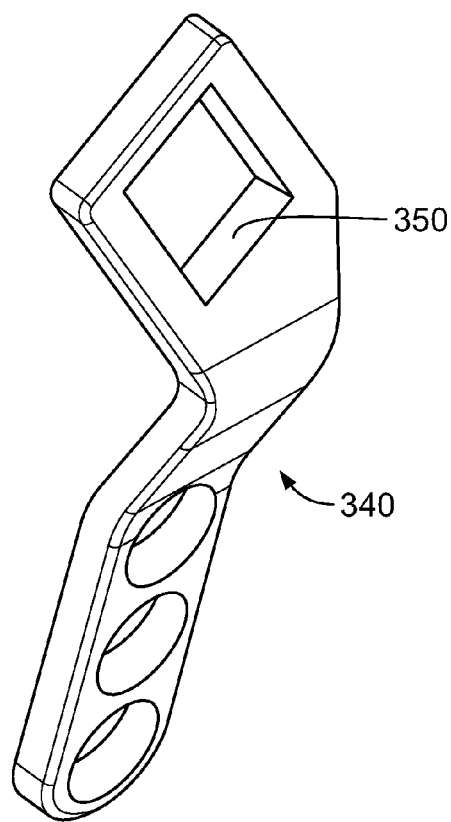
FIG. 19 is a view of the tibial component shown in FIG. 18.
Figure 20A:
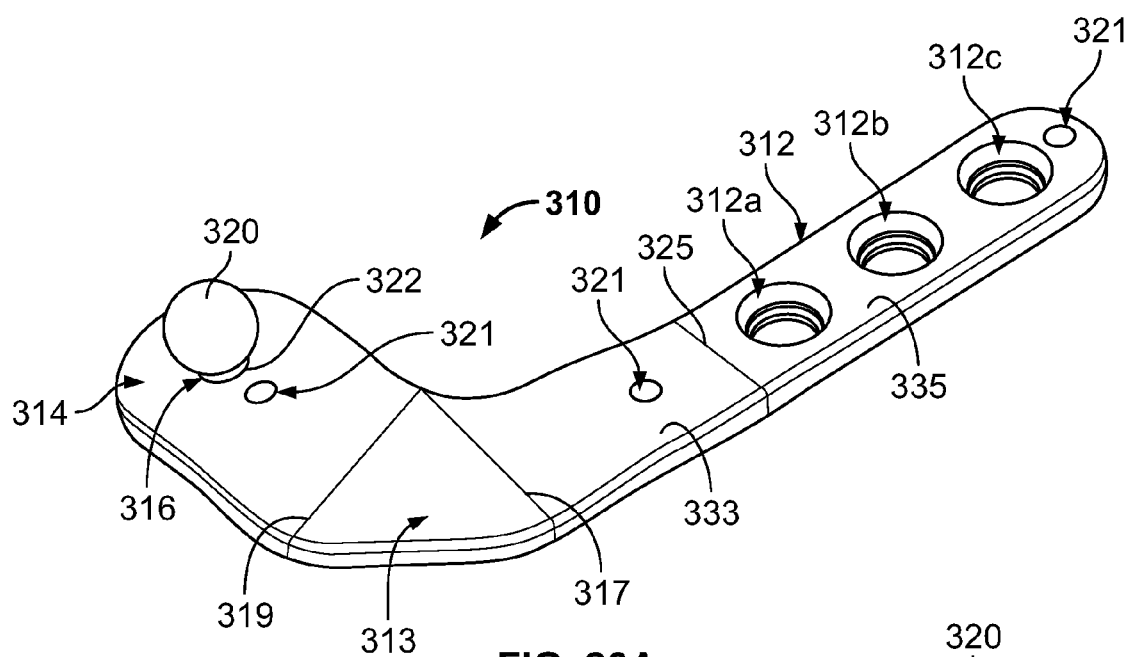
FIGS. 20A-20C are views of the femoral component shown in FIG. 18.
Figure 20B:
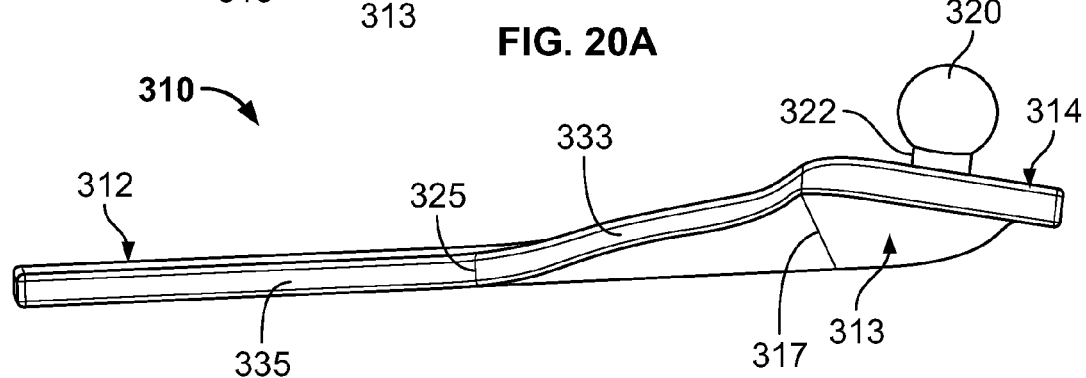
Figure 20C:
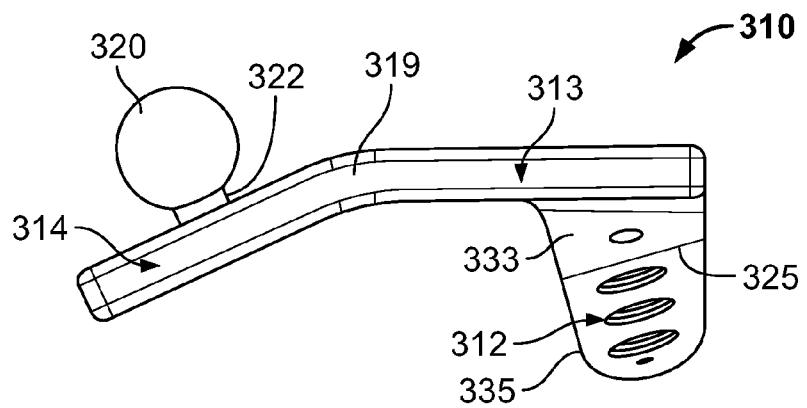

FIG. 18 is a perspective view of the assembled system. The system includes a femoral component 310, a tibial component 340, and an articular sliding insert component 360. FIG. 19 is a view of the tibial component 340, including a slot 350. FIGS. 20A-20C are views of the femoral component 310. Femoral component 310 includes a leg portion 312, a bottom portion 314, and an intermediate portion 313. The leg portion 312 further comprises a first leg portion 333, and a second leg portion 335, the first and second leg portions 333 and 335 can be separated by a bend. The leg portion 312 and bottom portion 314 each form plane angles (e.g., in the same direction) with respect to the intermediate portion 313 therebetween, thereby forming a general hockey stick shape. The femoral component 310 could have a dihedral angle (e.g., first bend 317) between the first leg portion 312a and intermediate portion 313, and a dihedral angle (e.g., second bend 319) between the intermediate portion 313 and the bottom portion 314. The first bend 317 and second bend 319 being in the same direction.

Further, the bend between first leg portion 312a and second leg portion 312b could have a dihedral angle (e.g., third bend 325). The third bend 325 could be in a different direction from the first bend 317 and second bend 319. Further, the first leg portion 312a could have an axial twist (e.g., along a length of the first leg portion 312a). In other words, the end of the first leg portion proximate the first bend 317 could be oriented on a different axis than the end of the first leg portion proximate the third bend 325. The axial twist could be through the center of the first leg portion 312a or along an edge of first leg portion 312a (e.g., along an outer edge of first leg portion 312a).

The femoral component 310 contains attachment holes 312a, 312b, and 312c in second leg 312b and an aperture 316 in bottom portion 314. The femoral component 310 could further comprise a ball 320 and stem 322 in bottom portion 314 of the femoral component 310. The stem 322 is received by aperture 316, and the ball 320 extends outward from the outer surface of the bottom portion 314 of the femoral component 310 at approximately 90 degrees. The femoral component 310 further comprises one or more temporary attachment holes 321, which could vary in number and location. The temporary attachment holes 321 could be used for temporary fixation with a surgical tool or temporary surgical implant (e.g., holding pins, k-wire, etc.). As shown, one temporary attachment hole 321 can be located at an end of the leg 312 (proximate attachment hole 312c, but not proximate attachment hole 312b), and another temporary attachment hole 321 can be proximate the stem 322. Further, the femoral component 310 could utilize locking technology (e.g., locking screws and locking attachment holes 312a, 312b and 312c).

Figure 21A:
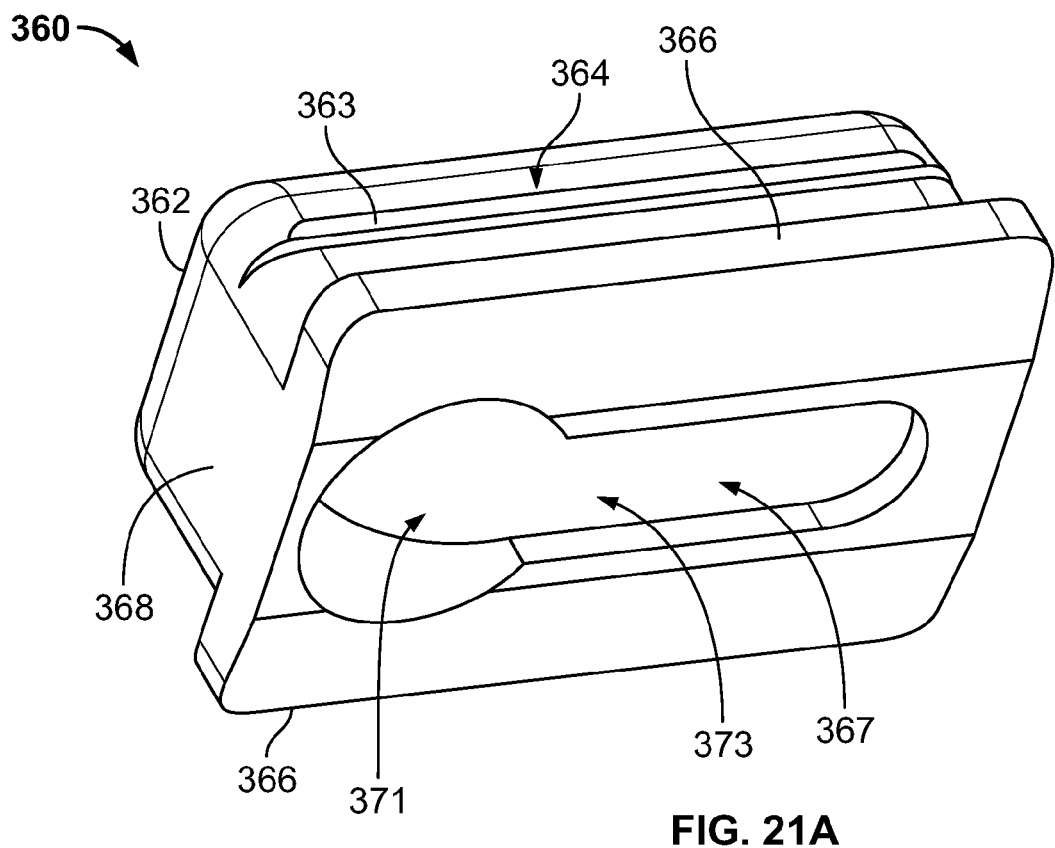
FIGS. 21A-21B are views of the articular sliding insert component shown in FIG. 18.
Figure 21B:
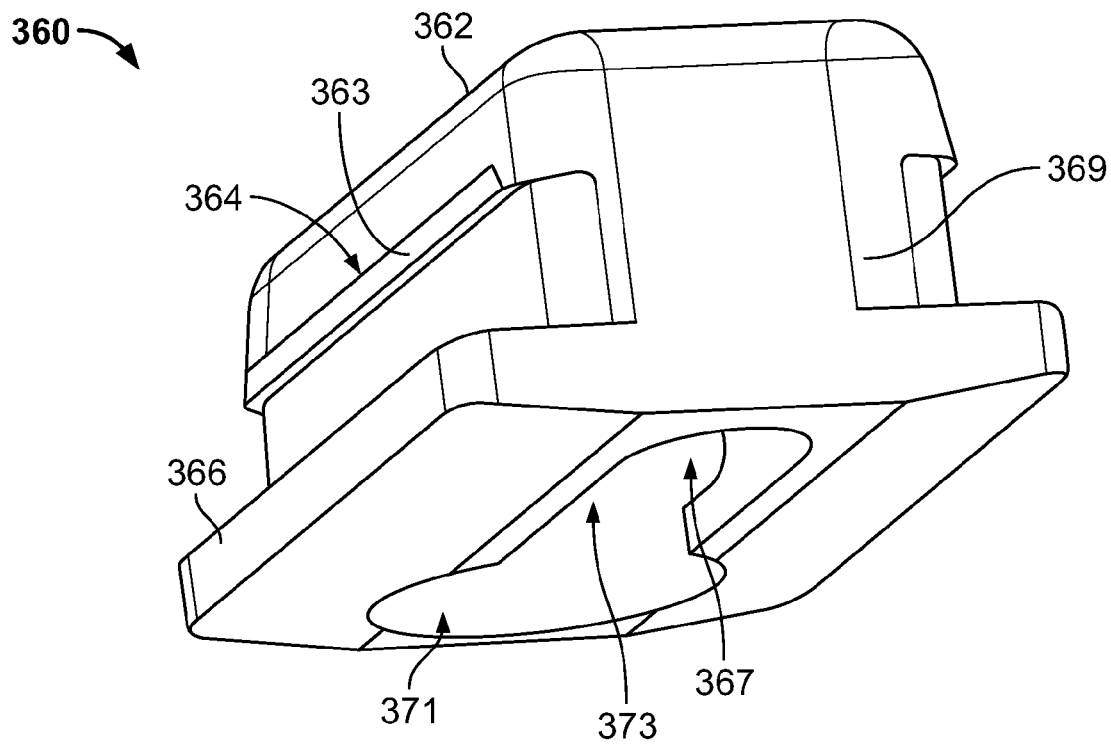

FIGS. 21A-21B are views of the articular sliding insert component 360. The articular sliding insert component 360 comprises a generally rectangular-shaped component that conforms to, and is received by, the rectangular opening of the proximal tibial component, as discussed in relation to FIGS. 4A-4C and 14 above. The articular sliding insert component 360 has a top 362, side walls 364, rear wall 369 and front wall 368, defining a housing with an open interior. The bottom surface includes lower angled flange extensions 366 extending outwardly from the lower portion of sidewalls 364, and upper shoulder extensions 363. The insert component 360 could be inserted in slot 350 of tibial component 340, and then secured therein by shoulders 363, and flanges 366.

The articular sliding component 360 further comprises a central channel 367. The central channel 367 is generally cylindrically shaped and extends along the length of the insert component 360. The end of the central channel 367 proximate the front wall includes an enlarged opening 371 extending through the bottom of the insert component 360. The ball 320 of the femoral component 310 can be inserted into the central channel 367 of the articular sliding component 360 through the enlarged opening 371. The ball 320 can move along the central channel 367 and is retained in the central channel 367 by the bottom of the insert component 360. A bottom opening 373 (e.g., slot) in the bottom of the insert component 360 extending from the enlarged opening 371 allows the stem 322 to move along the channel 367 with the ball 320. Once inserted, there is sufficient room to provide lateral movement for the stem 322, but insufficient room for the ball 320 to detach from the insert component 360 (other than through the enlarged opening 371). The channel 367 could extend from proximate the front wall 368 for at least a portion toward the rear wall 369 (proximate the rear wall 369). In other words, the channel could be closed at one end by the rear wall 369 and closed at the other end by the front wall 368.

Having thus described the system and method in detail, it is to be understood that the foregoing description is not intended to limit the spirit or scope thereof. It will be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure.

The invention claimed is:

1. A stifle stabilization system, comprising:
   a femoral component having a leg portion and bottom portion, the bottom portion including an interconnected coupling member protruding therefrom;
   an articular sliding insert component having a channel corresponding in size and shape to at least part of the coupling member, an enlarged opening in a bottom surface of the insert component in communication with the channel, and a slot through the bottom surface of the insert component in communication with the enlarged opening and the channel, the channel receiving the at least part of the coupling member through the enlarged opening; and
   a tibial component having a first proximal planar portion defining a slot, the slot being of corresponding and complementary shape to the articular sliding insert component to receive the articular sliding insert component therein.

2. The system of claim 1, wherein the system, when surgically implanted, stabilizes an unstable quadruped stifle joint during movement.

3. The system of claim 1, wherein the leg portion of the femoral component includes attachment holes for attachment to a femur.

4. The system of claim 1, wherein the femoral component conforms and is permanently attached to a contour of a medial third of a distal femur.

5. The system of claim 1, wherein the femoral component conforms and is temporarily attached to a contour of a medial third of a distal femur.

6. The system of claim 1, wherein the leg portion and bottom portion form a plane angle with respect to one another.

7. The system of claim 1, wherein the leg portion and bottom portion form a dihedral angle with respect to one another.

8. The system of claim 1, wherein the leg portion and bottom portion form plane angles with respect to an intermediate portion therebetween.

9. The system of claim 1, wherein the leg portion and bottom portion form dihedral angles with respect to an intermediate portion therebetween.

10. The system of claim 1, wherein the leg portion comprises a first leg portion and a second leg portion, the first and second leg portions form dihedral angles with respect to one another, and wherein the first leg portion is twisted along an axis thereof.

11. The system of claim 10, wherein the coupling member is pressure fit into the aperture.

12. The system of claim 1, wherein the slot further defines a recess corresponding in size and shape to the at least part of the coupling member of the femoral component.

13. The system of claim 1, wherein the coupling member comprises a ball and stem.

14. The system of claim 13, wherein the stem extends through the slot and the ball is retained within the channel.

15. The system of claim 1, wherein the tibial component conforms and is attached to contours of a proximal medial tibia.

16. The system of claim 15, wherein the first proximal planar portion is angled with respect to the second proximal planar portion, and the second and third proximal planar portions are aligned.

17. The system of claim 15, wherein the third distal planar portion of the tibial component contains attachment holes for attachment to a tibia.

18. The system of claim 1, wherein the tibial component has a first proximal planar portion and a third distal planar portion that form dihedral angles with respect to a second central planar portion therebetween.

19. The system of claim 1, wherein the articular sliding insert component further comprises a lower angled flange extensions protruding outwardly from the lower portion of sidewalls, and an upper shoulder extensions, wherein when the tibial component is inserted into the slot of the tibial component, the tibial component is secured between the flange extensions and shoulder extensions of the articular sliding insert component.

20. A stifle stabilization system, comprising: a femoral component having one or more attachment holes and a coupling member extending therefrom; an articular sliding insert component defining a channel corresponding in size and shape to at least part of the coupling member, the sliding component having on its bottom surface a bottom opening along the channel of the articular sliding component and including an enlarged opening through the bottom surface at an end of the bottom opening along the channel, the enlarged opening sized to receive at least a portion of the coupling member therethrough; and a tibial component having one or more attachment holes and defining a slot, the slot being of corresponding and complementary shape to the articular sliding insert component to receive the articular sliding insert component therein.

21. The system of claim 20, wherein the femoral component conforms to contours of a femur.

22. The system of claim 20, wherein the tibial component conforms to contours of a tibia.

23. The system of claim 20, wherein the leg portion comprises a first leg portion and a second leg portion, the first and second portion form dihedral angles with respect to one another, and wherein the first leg portion is twisted along an axis thereof.

* * * * *